United States Patent [19]

Hunter

[11] Patent Number: 4,966,340
[45] Date of Patent: Oct. 30, 1990

[54] WHEELED STAND APPARATUS FOR HANGING CONTAINERS OF MEDICAL FLUIDS

[76] Inventor: Rebecca L. Hunter, 157 Avenida Veracruz, Anaheim Hills, Calif. 92808

[21] Appl. No.: 342,733

[22] Filed: Apr. 24, 1989

[51] Int. Cl.⁵ ............................................. F16M 1/04
[52] U.S. Cl. ........................................ 248/125; 5/503; 5/507
[58] Field of Search .............................. 248/125, 129; 280/304.1, 304.5, 288.4; 403/100, 102; 5/503, 507, 508, 510

[56] References Cited

U.S. PATENT DOCUMENTS

| | | | |
|---|---|---|---|
| 1,906,218 | 4/1933 | Patchell | 403/100 |
| 4,351,505 | 9/1982 | Wickershan | 248/316.8 X |
| 4,511,157 | 4/1985 | Wilt, Jr. | 248/125 X |
| 4,600,209 | 7/1986 | Kerr, Jr. | 5/503 X |
| 4,642,931 | 2/1987 | Flores | 403/100 X |
| 4,691,397 | 9/1987 | Netzer | 5/507 |
| 4,725,027 | 2/1988 | Bekanich | 248/125 |
| 4,744,536 | 5/1988 | Bancalari | 248/125 |

Primary Examiner—David L. Talbott
Assistant Examiner—Daniel Hulseberg
Attorney, Agent, or Firm—Gary Appel

[57] ABSTRACT

An intravenous stand apparatus for carrying medical fluids, such as blood plasma or saline solutions, in a manner enabling the fluids to be gravity flowed into a patient comprises a base; a plurality of wheels mounted to the base to enable the rolling thereof along a floor or the like; and an elongate, slender support member having one or more hooks at its upper end to enable the hanging of fluid-dispensing containers therefrom. The lower end of the support member is hinged to the base in a manner enabling the support member to be pivoted between a first, upright position in which the support member is perpendicular to the base, and a second, folded position in which the support member is parallel to the base. A sliding tube is mounted around the support member for releasably locking the support member in the first, upright position. A spring loaded detent is provided for releasably retaining the sleeve in its locking position. The apparatus further comprises a bracket adapted for being attached to a gurney, hospital bed, and the like, and for receiving the base when the base is in a substantially vertical condition, a releasable clip being provided for releasably locking the support member to the gurney, hospital bed, and the like, so that the support member is in the upright proper position for enabling the delivery of medical fluids to a patient on the gurney, hospital bed, and the like.

9 Claims, 2 Drawing Sheets

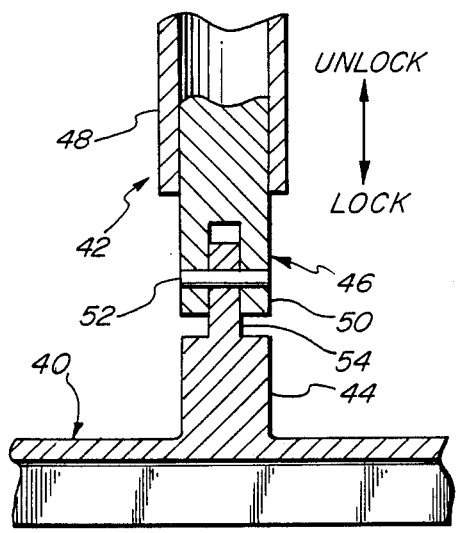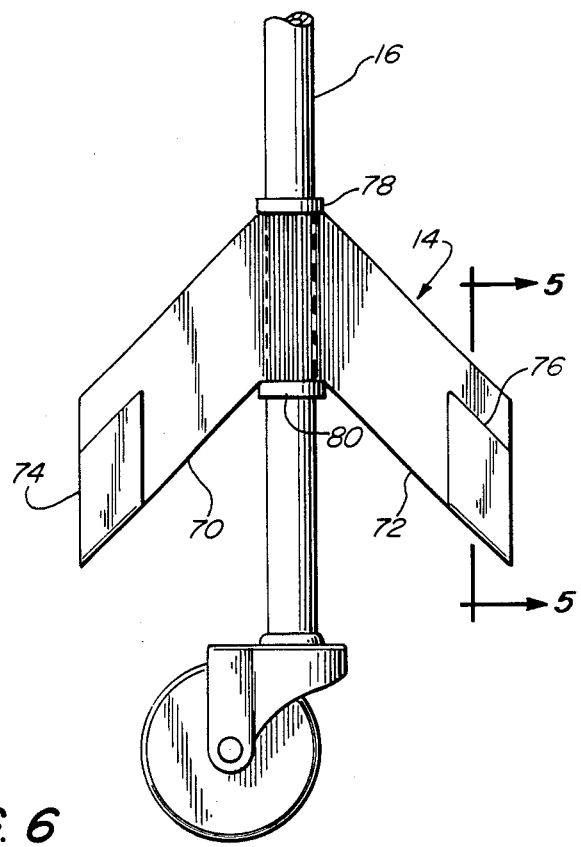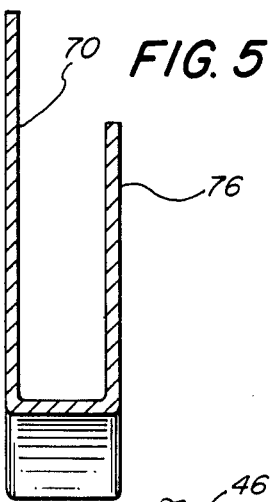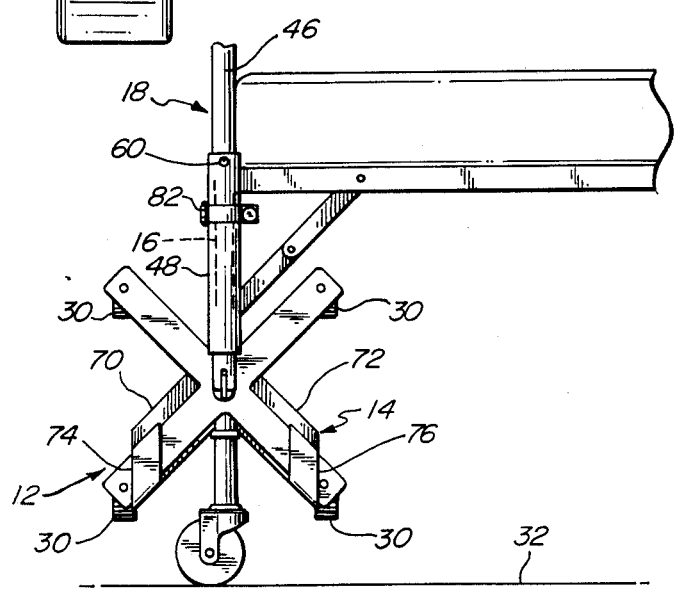

WHEELED STAND APPARATUS FOR HANGING CONTAINERS OF MEDICAL FLUIDS

BACKGROUND OF THE INVENTION

1. Field of the Invention:

The present invention relates generally to the field of medical equipment and, more particularly, to wheeled stands from which containers of medical fluids, such as saline solutions, blood plasma, and other intravenous fluids, are hung to enable gravity flowing of the fluids to a patient; and which are, for example, typically wheeled along with patients who are transported on a hospital gurney into and from operating rooms, patient's rooms, and so forth.

2. Discussion of the Background:

Anyone who has ever been a patient or a visitor in a hospital, or who has ever watched medical programs or even news broadcasts on television, is familiar with hospital procedures in which patients are moved about hospitals, for example, into operating rooms and trauma centers, on small wheeled tables commonly known as gurneys. Equally familiar is the sight of nurses or other patient attendants following—often running in emergency situations—along with gurneys pushing a tall wheeled stand on which are hung one or more bottles or plastic pouches containing life sustaining fluids, such as blood plasma and saline solutions, which are connected to a patient on the gurney by a flexible plastic tube or tubes. Commonly, these stands with their intravenous fluid containers remain with the patient when the patient is transferred from the gurney onto an operating table or from the gurney into a hospital bed.

These stands, which may be referred to as IV (intravenous) stands, resemble an old fashioned hat rack on wheels, being constructed having a tall, slender, upright post or pole mounted onto a relatively small-sized base usually having four small wheels. The post or pole is fitted with a hanger from which the bottles or pouches of medical fluids are hung.

Because IV stands must be kept close to their associated gurneys, and because gurneys and IV stands must frequently be moved rapidly along sometimes congested corridors and must often be manipulated in operating rooms with limited space and/or with numerous doctors, nurses, and technicians hurrying about, it is necessary that the base portions of IV stands be made relatively small. Otherwise, people would be likely to trip over the bases and the stands would be even more in the way. However, larger IV stand bases would be more likely to be accidently kicked and the stand knocked over.

On the other hand, because IV stand bases are typically made relatively small, the stands are relatively unstable and can be knocked over rather easily, particularly in emergency situations when individuals attending a patient are getting in one another's way and attention is being given to caring for the patient and not so much to keeping the IV stand stable. In this regard, it can be appreciated that an IV stand must always be more or less in unison with its associated gurney. If the stand does not keep up with the moving gurney, the stand may be tipped over by the pull on it by the fluid tubes attached to the patient on the gurney. Alternatively, the pull on the fluid tubes may cause feeding needles attached to the tubes to be pulled out of the patient on the gurney.

Still other problems can occur when the IV stand is placed near a patient's bed in a hospital room. Because of the stand's small base, the stand may be easily tipped over by movement of the attached patient, accidently pulling on the feeding tubes. Yet another problem is encountered with patients who must be connected to an IV solution container, even when the patient is otherwise in condition to be moved around in a wheelchair. In such situations, an attendant is required just to wheel the IV stand around with the patient—thereby adding to patient charges and tying up hospital personnel.

For these and other reasons, improvements are needed to IV stands to make them safer and more convenient to use, and to increase patient safety and reduce hospital costs. It is a principal object of the present invention to provide such improved IV stand improvements.

SUMMARY OF THE INVENTION

In accordance with the present invention there is, therefore, provided an IV stand apparatus for carrying medical fluids, such as blood plasma and saline solutions, in a manner to be gravity flowed into a patient. The stand apparatus comprises a base; a plurality of wheels mounted to the base to enable the rolling thereof along a floor or the like; an elongate, slender support member having means at an upper end region to enable the hanging of fluid-dispensing containers therefrom; and hinge means for connecting the lower end of the support member to the base in a manner enabling the support member to be pivoted between a first, upright position in which the support member is perpendicular to the base, and a second, folded position in which the support member is parallel to the base. Also included in the apparatus are means for releasably locking the support member in the first, upright position.

According to the preferred embodiment, the support member comprises a slender, rigid rod or tube, and the locking means comprise an elongated sleeve sized to slide along the support member and down over the hinge means when the support member is in the first, upright position, the pivoting of the support member from the first, upright position being hereby prevented. Also in accordance with the preferred embodiment, there are included means for releasably locking the sleeve in the position in which the sleeve is slid over the hinge means, so as to prevent the accidental unlocking of the support member.

It is preferred that the apparatus further comprise bracket means adapted for being attached to a rail of a gurney, hospital bed, and the like, and for receiving the base when the base is in a substantially vertical condition so that the apparatus is carried along with the gurney, hospital bed and the like. There are then included means for releasably locking the support member to such leg when the base is received into the bracket means and when the support member is in the second, folded position relative to the base. In such case, the support member is in an upright condition relative to the gurney, hospital bed and the like, and is in the proper position for enabling the delivering of medical fluids to a patient on the gurney, hospital bed and the like.

BRIEF DESCRIPTION OF THE DRAWINGS

The present invention can be more readily understood from the following detailed description, when taken in conjunction with the accompanying drawings, in which:

FIG. 3 is a vertical cross sectional view taken along line 3—3 of FIG. 2, showing details of the manner in which the support member is hinged to the base;

FIG. 4 is a front view of the bracket for holding the base of the IV stand to a gurney or the like, when the support member is in a folded condition relative to the base;

FIG. 5 is a vertical cross-sectional view taken along line 5—5 of FIG. showing details of the IV stand base holding bracket; and FIG. 6 is a front view showing the IV stand held by the bracket of FIG. 4 to a gurney or the like.

When the same elements and features are shown in more than one FIG., they are given the same reference numbers in all such FIGS.

DESCRIPTION OF THE PREFERRED EMBODIMENT

Figures 1, 2:
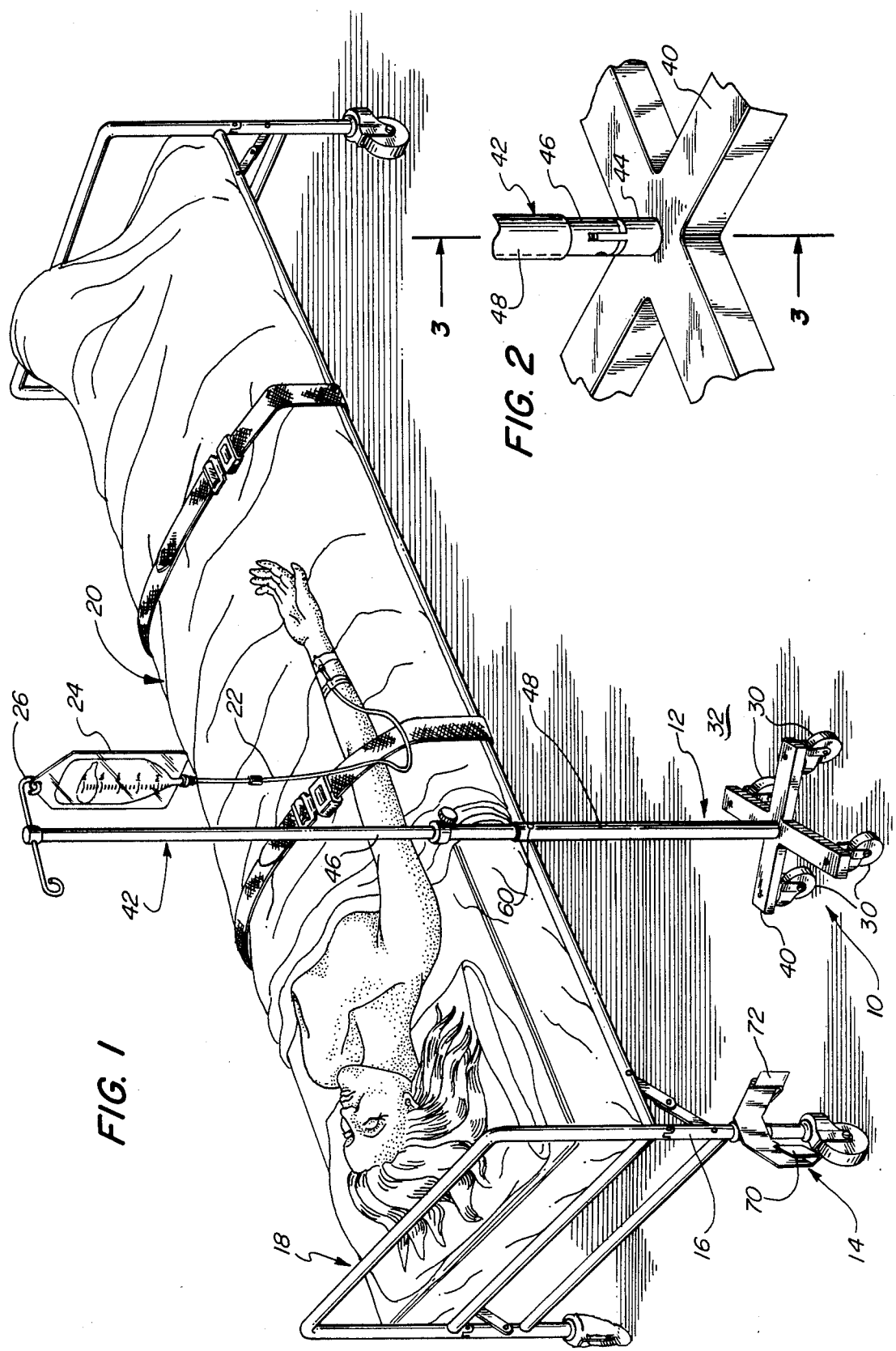
FIG. 1 is a perspective drawing of an improved IV stand apparatus in accordance with the present invention showing the stand in a first condition in which an elongate, upright support member of the stand is perpendicular to a horizontal stand base and showing wheels of the base on the floor, and still further showing the IV stand being used in conjunction with a hospital gurney having mounted to one leg thereof a bracket for holding the stand base in a vertical position when the support member is in a folded condition relative to the base.
FIG. 2 is a partial perspective drawing showing the hinging of the support member of the IV stands to the base.

Shown in FIG. 1 is an IV stand apparatus, in accordance with the present invention, which comprises generally a partially foldable IV stand 12 and a stand attaching bracket 14, the latter of which is shown mounted to a leg 16 of a conventional hospital gurney 18. By way of illustration, a patient 20 is shown lying on gurney 18 and is shown receiving, through a flexible tube 22, fluid from a bottle or container 24 hung from a hook or other means 26 at the top of IV stand 12. It is to be appreciated that although for purposes of illustrating the present invention, bracket 14 is shown in FIG. 1 as being attached to a gurney 18, the invention is not limited thereto. For example, bracket 14 can alternatively be attached to a hospital bed, wheel chair or the like so that stand 12 can be supported thereon.

As is more particularly described below, IV stand 12 can be used in a conventional manner (as depicted in FIG. 1) in which wheels or casters 30 of the stand rest upon a floor 32, and wherein the stand is moved separately from gurney 18. Alternatively (as depicted in FIG. 6), IV stand 12 can be supported from gurney 18 so as to be carried along therewith whenever the gurney is moved.

More specifically, IV stand 12 comprises a generally X-shaped base 40 and a slender, elongate upright support member 42, which is hinged to an upwardly projecting portion 44 of the base (FIGS. 2 and 3) for movement between a first position (FIG. 1) in which the support is perpendicular to the base, and a second position (FIG. 6) in which the support is parallel to the base.

As seen from FIGS. 1-3, support 42 comprises an elongate, slender, yet rigid rod (or tube) 46, around which is slidingly disposed a tubular locking sleeve 48. The lower, forked end 50 of rod 46 is pivotally connected by a transverse pin 52, to an upper end region 54 of base portion 44 (FIG. 3). Pin 52, which may be a conventional roll pin, enables support 42 to pivot relative to base 40 between the above-mentioned first position in which the support is perpendicular to the base, and the second position in which the support is parallel to the base. Preferably base portion 44 is short enough so that in the second position, support 42 is folded closely to the base.

Rod 46 and base portion 44 are circular in cross-section and have the same outer diameter. Locking sleeve 48 has an outside diameter permitting it to slide closely down over the pinned connection between rod 46 and base portion 44, to thereby prevent the pivoting of support 42 relative to base 40. In this manner, support member 42 is locked in its first, perpendicular position depicted in FIG. 1. A releasable spring-loaded detent 60 (FIG. 1) of a known type, releasably retains locking sleeve 48 in its lowermost position, which keeps support 42 in the perpendicular position (relative to base 40). When detent 60 is released and locking sleeve 48 is slid back upwardly so as to clear the connection between rod 46 and base portion 44 (FIGS. 2 and 3), support 42 is unlocked, and thus can be pivoted to its second, parallel position relative to base 40 (FIG. 6)

It will be appreciated that with support member 42 locked, by sleeve 48, in its upright position, IV stand 12 may be used in the manner of conventional IV stands. That is, IV stand 12 may be wheeled around by itself or in association with a gurney or the like. In contrast, however, to a conventional IV stand, stand 12 of the present invention may be alternatively mounted to gurney 18 in the manner described below, and may accordingly be transported directly with the gurney.

Bracket 14, as shown in FIGS. 1 and 4-6, is formed generally in the shape of an inverted V and is preferably formed out of sheet metal. Comprising bracket 14 are flat, left and right downward sloping legs 70 and 72, which are coplanar and which are formed at 90° relative to each other or otherwise, to match the angle between leg portions of base 40 (FIG. 4). Formed at the free ends of legs 70 and 72 are respective U-shaped hangers 74 and 76, which are sized to receive base 40 when the base is vertically oriented (that is, when the base is parallel with the bracket), and which support the base (FIGS. 4-6).

Included as part of the bracket 14 are respective upper and lower clamps 78 and 80, by means of which the bracket is detachably attached to gurney leg 16 (FIG. 4) at a height elevating received base 40 above surface 32 onto which gurney 18 rests.

In order to mount IV stand 12 to gurney 18, bracket 14 is attached to gurney leg 16 in the above-described manner. Locking sleeve 48 is raised and the support member is pivoted to its second position parallel to base 40, the base being then merely inserted downwardly into bracket hangers 74 and 76. A separate clamp 82 (FIG. 6) is then passed around support member locking sleeve 48 and gurney leg 16 to releasably secure support member 18, and hence, the entire IV stand 12 to gurney 18 with the support member in a vertical position. If locking sleeve 48 is too short to be clamped to gurney leg 16 in the manner described, then clamp 82 is passed directly around support member 42 and gurney leg 16.

Although there is described above a specific embodiment of an intravenous stand apparatus according to the present invention for the purposes of illustrating the manner in which the invention may be used to advantage, it is to be appreciated that the invention is not limited thereto. Accordingly, any and all modifications and variations which may occur to those skilled in the art are to be considered to fall within the scope and spirit of the invention as defined by the appended claims.

What is claimed is:

1. A stand apparatus for carrying medical fluids, such as blood plasma and saline solutions, in a manner enabling the fluids to be gravity flowed into a patient, said stand apparatus comprising:
   a. a base;
   b. a plurality of wheels mounted to said base to enable the rolling thereof along a floor or the like;
   c. an elongate, slender support member having means at an upper end region to enable the hanging of fluid dispensing containers therefrom;
   d. hinge means for connecting the lower end of the support member to the base in a manner enabling the support member to be pivoted between a first, upright position in which the support member is perpendicular to the base, and a second, folded position in which the support member is parallel to the base; and,
   e. bracket means adapted for being attached to a leg of a gurney, hospital bed, and the like and for receiving said base when the base is in a substantially vertical condition.

2. The stand apparatus as claimed in claim 1, wherein the support member comprises a slender, rigid rod or tube, and including first means for releasably locking the support member in the first, upright position, the first locking means comprising an elongate sleeve sized to slide along said support member and down over said hinge means when the support member is in the first, upright position to thereby prevent the pivoting of the support member from the first, upright position.

3. The stand apparatus as claimed in claim 2, including second means for releasably locking said sleeve in the position in which the sleeve is slid over the hinging means.

4. The stand apparatus as claimed in claim 1, including third means for releasably locking said support member to said leg when the base is received into said bracket means and when the support member is in the second, folded position relative to said base, the support member then being in an upright condition relative to said gurney, hospital bed, and the like.

5. A stand apparatus for carrying medical fluids, such as blood plasma and saline solutions, in a manner enabling the fluids to be gravity flowed into a patient, said apparatus comprising:
   a. a base;
   b. a plurality of wheels mounted to said base to enable the rolling thereof along a floor or the like;
   c. an elongate slender support member having means at an upper end region to enable the hanging of fluid-dispensing containers therefrom;
   d. hinge means for connecting the lower end of the support member to the base in a manner enabling the support member to be pivoted between a first, upright position in which the support member is perpendicular to the base and a second, folded position in which the support member is parallel to the base; and
   e. bracket means adapted for being attached to a gurney, hospital bed and the like, and for receiving said base when the base is in a substantially vertical condition;
   f. first means for releasably locking the support member in the first, upright position; and
   g. second means for releasably locking the first locking means in position.

6. The stand apparatus as claimed in claim 5, including third means for releasably locking said support member to said gurney, hospital bed, and the like when the base is received into said bracket means and when the support member is in the second, folded position relative to said base, the support member then being in an upright condition relative to said gurney, hospital bed, and the like.

7. A stand apparatus for carrying medical fluids, such as blood plasma and saline solutions, in a manner enabling the fluids to be gravity flowed into a patient, said apparatus comprising:
   a. a base;
   b. a plurality of wheels mounted to said base to enable the rolling thereof along a floor or the like;
   c. an elongate slender support member comprising a rigid rod or tube and having means at an upper end region to enable the hanging of fluid-dispensing containers therefrom; and
   d. hinge means for connecting the lower end of the support member to the base in a manner enabling the support member to be pivoted between a first, upright position in which the support member is perpendicular to the base and a second, folded position in which the support member is parallel to the base;
   e. first means for releasably locking the support member in the first, upright position, said locking means comprising an elongate sleeve sized to slide along said support member and down over said hinge means when the support is in the first, upright position to thereby prevent the pivoting of the support member form the first, upright position;
   f. second means for releasably locking said sleeve in the position in which the sleeve is slid over the hinging means; and
   g. bracket means adapted for being attached to a gurney, hospital bed and the like, and for receiving said base when the base is in a substantially vertical condition.

8. The stand apparatus as claimed in claim 7, including third means for releasably locking said support member to said gurney, hospital bed, and the like when the base is received into said bracket means and when the support member is in the second, folded position relative to said base, the support member being then in an upright condition relative to said gurney, hospital bed, and the like.

9. Claim 9. A stand apparatus for carrying medical fluids, such as blood plasma and saline solutions, in a manner enabling the fluids to be gravity flowed into a patient, said stand apparatus comprising:
   a. a base;
   b. a plurality of wheels attached to said base to enable the rolling thereof along a floor or the like;
   c. an elongate, slender support member comprising a rigid rod or tube and having means at an upper end region to enable the hanging of fluid-dispensing containers therefrom;
   d. hinge means for connecting the lower end of the support member to the base in a manner enabling the support member to be pivoted between a first, upright position in which the support member is perpendicular to the base, and a second, folded position in which the support member is parallel to the base;

e. first means for releasably locking the support member in the first, upright position, said first locking means comprising an elongate sleeve sized to slide along said support member and down over said hinge means when the support member is in the first, upright position, to thereby prevent the pivoting of the support member from the first, upright position;

f. a second means for releasably locking said sleeve in the position in which the sleeve is slid over the hinging means;

g. bracket means adapted for being attached to a leg of a gurney, hospital bed, and the like and for receiving said base when the base is in a substantially vertical position; and, h. third means for releasably locking said support member to said leg when the base is received into said bracket means and when said support member is in the second folded position relative to said base, the support member being in an upright condition relative to said gurney, hospital bed, and the like.

* * * * *